United States Patent [19]

Hogan et al.

[11] Patent Number: 4,493,715
[45] Date of Patent: Jan. 15, 1985

[54] REMOVAL OF CARBON DIOXIDE FROM OLEFIN CONTAINING STREAMS

[75] Inventor: John P. Hogan; Charles R. Nease, both of Bartlesville, Okla.

[73] Assignee: Phillips Petroleum Company, Bartlesville, Okla.

[21] Appl. No.: 595,134

[22] Filed: Mar. 30, 1984

Related U.S. Application Data

[63] Continuation of Ser. No. 451,291, Dec. 20, 1982, abandoned.

[51] Int. Cl.$^3$ .............................................. B01D 53/04
[52] U.S. Cl. ......................................... 55/68; 55/74; 423/230; 502/415
[58] Field of Search ...................... 55/68, 74; 423/230; 502/63, 405, 414, 415

[56] References Cited

U.S. PATENT DOCUMENTS

| | | | |
|---|---|---|---|
| 1,831,644 | 11/1931 | Adair et al. | 55/68 X |
| 1,982,223 | 11/1934 | Metzger et al. | 55/68 X |
| 2,935,294 | 1/1976 | Teller | 423/230 X |
| 3,078,637 | 2/1963 | Milton | 55/68 |
| 3,141,729 | 7/1964 | Clarke et al. | 55/68 X |
| 3,240,830 | 3/1966 | Dye | 260/669 |
| 3,517,484 | 6/1970 | Lee et al. | 55/73 |
| 3,557,025 | 1/1971 | Emerson et al. | 502/414 X |
| 3,619,130 | 11/1971 | Ventriglio et al. | 423/230 |
| 3,743,709 | 7/1973 | Shaw et al. | 55/74 X |
| 3,808,774 | 5/1974 | Teller | 55/74 X |
| 3,847,837 | 11/1974 | Boryta | 423/230 X |
| 3,865,924 | 2/1975 | Gidaspow et al. | 55/68 X |
| 3,867,113 | 2/1975 | Foster et al. | 55/68 X |
| 3,878,289 | 4/1975 | Beavon | 55/68 X |
| 3,880,618 | 4/1975 | McCrea et al. | 55/68 |
| 3,885,927 | 5/1975 | Sherman et al. | 55/68 |
| 3,943,226 | 3/1976 | Difford | 423/230 |
| 4,039,620 | 8/1977 | Netteland et al. | 423/230 |
| 4,059,418 | 11/1977 | Cull | 55/74 X |
| 4,234,752 | 11/1980 | Wu et al. | 585/640 |

FOREIGN PATENT DOCUMENTS 353195   10/1972   U.S.S.R. .................................. 55/68

OTHER PUBLICATIONS

Kirk–Othmer, Encyclopedia of Chemical Technology, 3rd Ed., vol. 4, 1978, pp. 732–736.
Kirk–Othmer, Encyclopedia of Chemical Technology, 3rd Ed., vol. 8, 1979, pp. 114–118.

*Primary Examiner*—Robert Spitzer

[57] ABSTRACT

A process for the removal of $CO_2$ from a gaseous stream containing at least one $C_2$ to $C_4$ olefin is provided comprising contacting said stream with a regenerable calcined alkali metal compound-treated alumina.

6 Claims, No Drawings

REMOVAL OF CARBON DIOXIDE FROM OLEFIN CONTAINING STREAMS

This application is a continuation of U.S. Ser. No. 451,291, filed Dec. 20, 1982, now abandoned.

This invention relates to a process for the removal of carbon dioxide from a gaseous stream containing at least one $C_2$ to $C_4$ olefin.

Alumina is a well known adsorbent in many chemical processes such as the polymerization of olefins, e.g. ethylene, for the removal of water and small concentrations of methanol, carbonyl-containing compounds, and peroxides.

However, the use of alumina has disadvantages that impair its effectiveness as an adsorbent. For example, alumina does not always work as an adsorbent for the removal of $CO_2$, a well known catalyst inhibitor, from gaseous olefin containing streams which contain $CO_2$ at low level concentrations (i.e. down to 1 ppm).

Molecular sieves are used as adsorbents for $CO_2$ but are inefficient when used for the removal of $CO_2$ from a gaseous stream containing low molecular weight olefins such as ethylene.

Caustic scrubbers or bulk caustic scrubbers can function as absorbents for $CO_2$ from a gaseous stream but have the disadvantages of being hazardous, non-regenerable, and adding water to the stream.

Therefore, an object of this invention is to provide a process for the removal of $CO_2$ from gaseous streams employing a regenerable adsorbent which removes even small amounts of $CO_2$.

Other aspects, objects, and the several advantages of the present invention are apparent from a study of this disclosure and the appended claims.

In accordance with the present invention, we have discovered that $CO_2$ can be efficiently removed from a gaseous stream containing a $C_2$ to $C_4$ olefin or mixtures thereof by contacting the stream with a regenerable adsorbent consisting essentially of a calcined alkali metal compound treated alumina. The removal of water, achieved by the use of alumina in general as known to one skilled in the art, is also within the scope of the present invention.

Although it is well known in the art to remove $CO_2$ from gaseous streams by means of solid caustic or caustic solutions (as indicated earlier in this disclosure) which convert $CO_2$ to an alkali metal carbonate such as $Na_2CO_3$, this does not occur in the present invention. Instead, $CO_2$ is chemisorbed on an alkali metal oxide (e.g. $Na_2O$) alumina surface and can be readily desorbed by mild heating and sweeping the adsorbent bed with a gas free of $CO_2$.

The present invention is not to be confused with the use of chemical processes which convert $CO_2$ to alkali metal carbonates in a non-regenerable process which adds water to the gas stream being processed (i.e. $2NaOH + CO_2 \rightarrow Na_2CO_3 + H_2O$). In the process of the present invention, $CO_2$ is removed by a regenerable alumina which at the same time can be used to remove traces of water from the process gas.

The gaseous stream treated in accordance with the present invention will contain a $C_2$ to $C_4$ olefin or mixtures thereof. Such olefins include ethylene, propylene, isobutylene, 1-butene and 2-butene.

The alumina employed in the present invention can be any alumina known in the art. Gamma and eta alumina are preferred and are typically employed.

Preferably the alumina employed will contain less than about 20 percent impurities such as $SiO_2$, $Na_2O$, $Fe_2O_3$, $TiO_2$ and $SO_4^=$.

Broadly the surface area of the alumina should be at least 50 $m^2/g$ or greater and preferably 200 $m^2/g$ or greater.

The alumina employed should contain from 1 to 6 weight percent Group IA alkali metal calculated as the oxide form. The level of alkali metal treatment will vary based on the particular alkali metal employed. Thus, when the alumina is treated with a lithium compound, the preferred level of lithium contacted with the alumina support is about 1 to about 3 weight percent calculated as $Li_2O$. When sodium is employed as the alkali metal, the range of about 2 to about 4 weight percent $Na_2O$ is preferred. When potassium is employed as the alkali metal, the treatment range of about 3 to about 6 weight percent $K_2O$ is preferred.

Typically the calcined alkali metal compound-treated alumina is prepared by contacting the alumina with a Group IA alkali metal compound dissolved in a suitable solvent such as water, alcohols, and esters. Water is preferred. Alkali metal compound-alumina contacting can be carried out in any suitable manner known in the art for solid-liquid contacting. For example, the techniques of incipient wetness or bulk solution can be employed. After sufficient contacting of the alumina and alkali metal compound containing solution, excess solution, if any, is removed by filtration, or decantation. Then the treated alumina is heated to a temperature from about 150° C. to about 700° C., preferably about 200° C. to about 400° C. Heating is maintained for about 1-24 hours, preferably about 5-10 hours under a gas flow of about 100-1000 GHSV. Suitable gases include $N_2$, air, natural gas stream, argon, and helium. Caution should be used with carbonaceous streams such as a natural gas stream to maintain the calcination temperature below about 300° C. to minimize formation of carbon deposits on the catalyst. When an oxygen containing gas is employed during catalyst preparation, it is desirable to purge the finished catalyst with an inert gas such as $N_2$, Ar, He, to ensure that oxygen is not introduced into the hydrocarbon feed stream. Although pressure is not critical, it is preferred to maintain the pressure during catalyst calcination near atmospheric or below to aid removal of gaseous species generated during the heating process.

Alkali metal compounds suitable for use in the present invention are soluble in the solvents disclosed previously, and are convertible under calcination conditions to the alkali metal oxide form, $M_2O$. Examples of suitable compounds include the hydroxide, nitrate, and acetate forms of the alkali metals. Hydroxides of lithium, sodium, and potassium are preferred because of their availability and cost.

The rate at which the olefin stream is fed to the adsorbent bed is not critical but will vary with reactor size. Broadly, the rate of olefin introduction will be about 1-15 WHSV (weight hourly space velocity), preferably about 5-8 WHSV. For a gaseous feed such as ethylene, the WHSV will vary as a function of the pressure employed. In any event, it should be at a rate sufficient to effect efficient contact between the feed and the treated alumina.

This invention is well suited for continuous reaction in which the olefin feed is continuously passed over a bed of calcined alkali metal compound-treated alumina at the desired reaction conditions.

Generally, the process of the present invention is carried out at a temperature of from about 0° C. to about 100° C. Presently preferred is a temperature in the range of from about 25° C. to about 50° C.

The pressure under which this invention is practiced will be from about atmospheric to about 1500 psig. Preferably, the pressure will be from about 400 to about 1000 psig with ethylene; atmospheric to about 130 psig with propylene; and atmospheric to about 30 psig for a butene stream.

In light of the effectiveness of the present invention, olefin streams containing as little as 1 ppm of an inhibitor such as $CO_2$ can be processed.

The calcined alkali metal compound-treated alumina may readily be regenerated by heating it in the presence of a gas stream such as $N_2$, He, Ar, air, or a natural gas stream. As described above, it is desirable to purge the regenerated catalyst bed with an inert gas such as $N_2$, He, or Ar prior to returning the catalyst to the process when an oxygen containing stream is used for catalyst regeneration.

A temperature of from about 150° C. to about 700° C., preferably about 200° C. to about 400° C. is employed until no further $CO_2$ and water vapor removal from the catalyst is achieved. Typically, regeneration takes about 1 to 24 hours, preferably 5-10 hours.

For typical plant scale operation, the inventive catalyst could be deployed in three packed beds such that at any given time one bed would be undergoing regeneration, and the other two beds in series would be contacting the olefin containing feed stream. As the first bed to contact the olefin containing feed stream becomes saturated with $CO_2$ (as evidenced by $CO_2$ in the effluent from the first bed), the backup catalyst bed would become the primary bed for contacting the olefin containing feed stream; the freshly regenerated bed would be put on stream as the backup catalyst bed, and the saturated bed would be treated under suitable regeneration conditions.

The following examples further illustrate the present invention.

EXAMPLES

Example I

Alumina Treatment

Adsorbents from a variety of supplies were employed:

| Supplier | Support Designation |
|---|---|
| Alcoa | H-151 $Al_2O_3$ |
| Alcoa | Z-100 $Al_2O_3$ |
| Kaiser | K-201 $Al_2O_3$ |
| Philadelphia Quartz Corp. | PQ 108 $SiO_2$ |
| Davison | Grade 979 $SiO_2/Al_2O_3$ |
| Linde | 5A Molecular Sieve |
| Linde | 13X Molecular Sieve |

The general procedure employed for treating alumina supports with an alkali metal compound was as follows. All alumina supports employed were crushed and sieved before use, 10-28 mesh particles being collected for use in the laboratory adsorption studies. The desired amount of hydroxide, such as sodium hydroxide, was dissolved in a volume of water just sufficient to wet the alumina thoroughly. The alumina adsorbent to be employed was then added to the alkali metal compound containing solution. The wet alumina support was then dried, such as by heating to above 100° C. for about 20 minutes or longer. Dry, alkali metal hydroxide treated adsorbent was typically activated by heating to about 260° C. for 5 hours in $N_2$ with flow maintained at about 40 L/hr.

For example, alumina adsorbent treated with enough sodium hydroxide to give 2.0% $Na_2O$ was prepared as follows. NaOH in the amount of 0.21 g was dissolved in 5 mL of water. To this solution, 8.0 g of Alcoa H-151 alumina was added with stirring. The wet alumina was heated in an evaporating dish to remove most of the excess water and then was activated at 260° C. for 5 hrs. under a 40 L/hr. nitrogen flow.

Example II

In a series of tests, 50–60 mg of activated adsorbent was placed on the pan of a Perkin-Elmer TGS-2 thermogravimetric analyzer (TGA), heated to 260° C. and held at 260° C. while being swept with helium at 1.5 SCFM until a constant weight was reached (indicating loss of moisture had ceased). The sample holder was then cooled to 30° C. in the helium stream and the sample weight was recorded. A helium-$CO_2$ mixture containing 10 mole percent $CO_2$ was then substituted for the helium stream, and the gain in weight due to $CO_2$ adsorption was followed until a constant weight was reached, usually within 30 minutes or less. The weight gain was recorded and the weight percent $CO_2$ loading was calculated. In some cases the adsorbent was regenerated by heating to 260° C. in helium and holding at 260° C. until weight loss ceased. The adsorbent was then recooled and the $CO_2$ adsorption experiment repeated. Results of these tests are shown in Table I.

TABLE I

| Description of Adsorbent | Promoter | | | % $CO_2$ Loading |
|---|---|---|---|---|
| | Ion | Concentration, as $M_2O$, % | | |
| | | Added | ~Total | |
| H-151 Alumina | Na | 0 | 2.7 | 2.0 |
| H-151 Alumina | Na | 1.4 | 4.1 | 2.3 |
| H-151 Alumina | Na | 2.0 | 4.7 | 2.7 |
| H-151 Alumina | Na | 2.8 | 5.5 | 2.9 |
| K-201 Alumina | Na | 0 | 0.3 | 1.6 |
| K-201 Alumina | Na | 2.8 | 3.1 | 2.9 |
| K-201 Alumina | Na | 4.2 | 4.5 | 3.4 |
| K-201 Alumina* | Na | 4.2 | 4.5 | 3.2 |
| K-201 Alumina | Na | 5.6 | 5.9 | 3.4 |
| K-201 Alumina | Li | 1.3 | 1.6 | 2.2 |
| K-201 Alumina | K | 3.2 | 3.5 | 2.4 |
| K-201 Alumina | K | 4.2 | 4.5 | 2.9 |
| 5A Mole Sieve | — | — | — | 12.2 |
| 13X Mole Sieve | — | — | — | 12.1 |
| PQ 108 Silica | Na | 0 | 0.1 | 0.4 |
| Davison $SiO_2/Al_2O_3$ | Na | 2.8 | 2.9 | 0.6 |
| NaOH | — | — | — | 12.5 |

After regeneration of adsorbent from previous run.

The data show that $CO_2$ adsorption capacity increased sharply when $Na_2O$ content of alumina was increased from sample to sample. The H-151 alumina, which originally contained about 2.7% $Na_2O$ as an impurity, and the K-201 alumina, which originally contained about 0.3% $Na_2O$, were almost equally effective in $CO_2$ adsorption when promoted with additional $Na_2O$. The $Li_2O$ and $K_2O$ promoted aluminas were also effective in adsorbing $CO_2$. In these experiments, the molecular sieves were quite effective in adsorbing $CO_2$ from helium, but were inefficient in the presence of ethylene, as shown in Example III. Silica and silica-alumina were less efficient than alumina. Bulk NaOH removed CO₂ but could not be regenerated.

Example III

A series of tests, designed to closely simulate conditions used in treating ethylene monomer with alumina in a polyethylene plant were conducted as follows. A 2-3 g sample of adsorbent to be tested, previously activated at 260° C., was transferred into a 1/8"×2½" brass pipe closed at each end with a needle valve. Ethylene, containing 11-17 ppm $CO_2$ (by volume) was passed through the adsorbent maintained at 700 psig at a rate of approximately 7 g per hour per g of adsorbent. The effluent ethylene was periodically sampled and analyzed for $CO_2$ as follows: The sample was injected into a Carle Model 211M chromatograph equipped with a 3/16"×22' Carbopack B column (80/100 mesh) operated at 50° C. A 60 mL/min He carrier gas stream carried the sample through the column and into a methanizer unit which converted the $CO_2$ to methane before being determined by a flame ionization detector. Sensitivity for $CO_2$ was less than 1 ppm. The ethylene flow and sampling were continued several days as necessary until $CO_2$ broke through the adsorbent and until the $CO_2$ concentration in the effluent approached that in the feed. The $CO_2$ concentration in the effluent was plotted against time, and the time to breakthrough and saturation determined. The total amount of $CO_2$ adsorbed was calculated and expressed as weight percent $CO_2$ loading on the adsorbent. Results are shown in Table II.

per lb of alumina, had to be regenerated about every 4 days to effect $CO_2$ removal when present at 5-6 ppm. The alumina was then removed and replaced with identical alumina to which had been added 3 weight percent $Na_2O$, added as a NaOH solution. At the same $CO_2$ concentration of 5-6 ppm in the ethylene, regeneration was now required only every 2 weeks.

This example shows that a calcined alkali metal compound treated alumina is considerably more effective for $CO_2$ removal than untreated alumina.

Reasonable variations and modifications are possible within the scope of the foregoing.

We claim:

1. A method for removing low concentrations of $CO_2$ from a gaseous olefin stream of at least $C_2$ to $C_4$ olefins which comprise passing said gaseous olefin stream containing $CO_2$ into contact with a regenerable, calcined adsorbent consisting essentially of from 1 to 6 weight percent of an alkali metal oxide selected from the group consisting of sodium, potassium and lithium on alumina, said regenerable, calcined adsorbent having been made by (a) contacting alumina with an alkali metal compound selected from the group consisting of sodium, potassium or lithium compounds which are convertible to the metal oxide on calcination, (b) drying the resulting alkali metal compound, treated alumina, and (c) thereafter calcining the dried treated alumina.

2. A process according to claim 1 wherein said olefin stream is ethylene and said alkali metal compound is one selected from the group consisting of hydroxides, nitrates and acetates of sodium, potassium and lithium.

TABLE II

| Run No. | Description of Adsorbent | Promoter Conc. as M₂O % Ion | Added | ~Total | Catalyst, g | Ethylene Feed Flow, L/Hr. | CO₂ (ppm) | Breakthrough, Hours | Saturation Hours | % CO₂ Loading |
|---|---|---|---|---|---|---|---|---|---|---|
| 1 | H-151 Alumina | Na | 0 | 2.7 | 2.7 | 20 | 11 | 26 | 63 | 0.7 |
| 2 | H-151 Alumina | Na | 1.0 | 3.7 | 2.6 | 15 | 15 | 41 | 88 | 1.1 |
| 3 | H-151 Alumina | Na | 1.4 | 4.1 | 2.1 | 12 | 15 | 48 | 78 | 1.2 |
| 4 | H-151 Alumina | Na | 2.0 | 4.7 | 2.8 | 16 | 14 | 65 | 107 | 1.3 |
| 5 | H-151 Alumina⁽¹⁾ | Na | 2.0 | 4.7 | 2.8 | 15 | 13 | 65 | 104 | 1.2 |
| 6 | H-151 Alumina | Na | 2.8 | 5.5 | 2.8 | 14 | 13 | 83 | 139 | 1.4 |
| 7 | K-201 Alumina | Na | 0 | 0.3 | 1.6 | 9 | 13 | 37 | 58 | 0.7 |
| 8 | K-201 Alumina | Na | 1.0 | 1.3 | 1.8 | 10 | 44 | 75 | 1.1 | |
| 9 | K-201 Alumina | Na | 2.0 | 2.3 | 2.2 | 12 | 13 | 115 | 146 | 1.8 |
| 10 | K-201 Alumina | Na | 2.8 | 3.1 | 2.0 | 11 | 15 | 88 | 128 | 1.7 |
| 11 | K-201 Alumina⁽²⁾ | Na | 2.8 | 3.1 | 2.0 | 11 | 15 | 102 | 132 | 1.9 |
| 12 | K-201 Alumina⁽²⁾ | Na | 2.8 | 3.1 | 2.0 | 11 | 14 | 94 | 123 | 1.7 |
| 13 | K-201 Alumina | Na | 4.2 | 4.5 | 2.0 | 11 | 15 | 91 | 122 | 1.7 |
| 14 | K-201 Alumina | Li | 2.7 | 3.0 | 1.9 | 11 | 14 | 87 | 144 | 1.8 |
| 15 | Z-100 Alumina | — | — | — | 2.4 | 13.5 | 14 | 42 | 75 | 0.9 |
| 16 | KOH | — | — | — | 3.0 | 17 | 14 | 31 | 67 | 1.0 |
| 17 | 5A Mole Sieve | — | — | — | 2.3 | 20 | 13 | ~3 | ~18 | 0.2 |
| 18 | 13X Mole Sieve | — | — | — | 2.0 | 11 | 13 | ~3 | ~18 | 0.2 |

⁽¹⁾Regeneration of catalyst from Run 4.
⁽²⁾Repeated regenerations of catalyst from Run 10.

From Table II it can be seen that sodium oxide promoted aluminas were far more effective than molecular sieves, which are frequently recommended by the adsorbent industry for $CO_2$ removal from gas streams. $Li_2O$ on alumina was also effective. KOH pellets, normally considered preferable to NaOH when used in bulk for $CO_2$ removal, were ineffective under these conditions (dry).

The optimum $Na_2O$ concentration proved to be in the range of 2-4 weight percent of the alumina.

Example IV

In a large polyethylene plant, alumina beds, used primarily to remove traces of moisture from ethylene at 700 psig and a flow ratio of 5-10 lbs ethylene per hour 3. A process according to claim 2 wherein said alkali metal compound is selected from the group consisting of lithium hydroxide, sodium hydroxide and potassium hydroxide.

4. A process according to claim 1 wherein said alkali metal oxide is lithium oxide and is present in an amount in the range of about 1 to about 3 weight percent.

5. A process according to claim 1 wherein said alkali metal oxide is sodium oxide and is present in an amount in the range of about 2 to about 4 weight percent.

6. A process according to claim 1 wherein said alkali metal is potassium oxide and is present in an amount in the range of about 3 to about 6 weight percent.

* * * * *